United States Patent
Al-Ali et al.

(10) Patent No.: US 7,438,683 B2
(45) Date of Patent: Oct. 21, 2008

(54) APPLICATION IDENTIFICATION SENSOR

(75) Inventors: Ammar Al-Ali, Tustin, CA (US); Massi E. Kiani, Laguna Niguel, CA (US); Walter M. Weber, Laguna Hills, CA (US)

(73) Assignee: Masimo Corporation, Irvine, CA (US)

( * ) Notice: Subject to any disclaimer, the term of this patent is extended or adjusted under 35 U.S.C. 154(b) by 537 days.

(21) Appl. No.: 11/071,875

(22) Filed: Mar. 3, 2005

(65) Prior Publication Data

US 2005/0283052 A1    Dec. 22, 2005

Related U.S. Application Data

(60) Provisional application No. 60/549,996, filed on Mar. 4, 2004.

(51) Int. Cl.
*A61B 5/00* (2006.01)

(52) U.S. Cl. .................. 600/309; 600/323

(58) Field of Classification Search ........... 600/310, 600/322, 323; 702/189
See application file for complete search history.

(56) References Cited

U.S. PATENT DOCUMENTS

| | | |
|---|---|---|
| 4,960,128 A | 10/1990 | Gordon et al. |
| 5,058,588 A * | 10/1991 | Kaestle ............. 600/323 |
| 5,163,438 A | 11/1992 | Gordon et al. |
| 5,337,744 A | 8/1994 | Branigan |
| 5,431,170 A | 7/1995 | Mathews |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan |
| 5,533,511 A | 7/1996 | Kaspari et al. |
| 5,590,649 A | 1/1997 | Caro et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |

(Continued)

*Primary Examiner*—Eric F Winakur
*Assistant Examiner*—Etsub D Berhanu
(74) *Attorney, Agent, or Firm*—Knobbe, Martens, Olson & Bear LLP

(57) ABSTRACT

An application identification sensor comprises a plurality of emitters configured to transmit light into a tissue site and a detector configured to receive the light after tissue absorption. The detector generates a signal responsive to the intensity of the light and communicates the signal to a monitor. An information element is readable by the monitor so as to identify a sensor application. The monitor presets at least one user-selectable operational parameter in response to the information element.

17 Claims, 1 Drawing Sheet

U.S. PATENT DOCUMENTS

| | | | |
|---|---|---|---|
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,044,283 A * | 3/2000 | Fein et al. | 600/310 |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,334,065 B1 | 12/2001 | Al-Ali et al. | |
| 6,349,228 B1 | 2/2002 | Kiani et al. | |
| 6,360,114 B1 | 3/2002 | Diab et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,515,273 B2 | 2/2003 | Al-Ali | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,591,123 B2 * | 7/2003 | Fein et al. | 600/323 |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,725,075 B2 | 4/2004 | Al-Ali | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Klani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |

* cited by examiner

APPLICATION IDENTIFICATION SENSOR

CROSS-REFERENCE TO RELATED APPLICATIONS

This application relates to and claims the benefit of prior U.S. Provisional Application No. 60/549,996 titled "Application Identification Sensor," filed Mar. 4, 2004 and incorporated by reference herein.

BACKGROUND OF THE INVENTION

Pulse oximetry is a widely accepted noninvasive procedure for measuring the oxygen saturation level of arterial blood, an indicator of a person's oxygen supply. A typical pulse oximetry system has a sensor, a monitor and a patient cable providing a communication path between the sensor and monitor. The sensor is adapted to attach to a tissue site, such as a patient's finger, and respond to hemaglobin constituents of pulsatile blood. The monitor is adapted to receive a physiological signal from the sensor and provide a numeric readout of the patient's oxygen saturation and pulse rate.

SUMMARY OF THE INVENTION

A conventional pulse oximetry monitor processes the physiological signal from the sensor based upon sensor calibration data, internal algorithm parameters and user-selectable operational parameters. The sensor may have an information element that is readable by the monitor and that identifies one or more characteristics of the sensor. These characteristics may relate to sensor components, such as emitter wavelength, or the sensor type, such as adult, pediatric or neo-natal. The monitor may select calibration data and internal parameters accordingly. An information element may be a passive device, such as a resistor, or an active device, such as a transistor network, a logic device or a memory chip. An information element is described in U.S. Pat. No. 5,758,644 entitled Manual and Automatic Probe Calibration, which is assigned to Masimo Corporation, Irvine, Calif. and incorporated by reference herein.

One aspect of an application identification sensor comprises a plurality of emitters configured to transmit light into a tissue site and a detector configured to receive the light after tissue absorption. The detector generates a signal responsive to the intensity of the light and communicates the signal to a monitor. An information element is readable by the monitor so as to identify a sensor application. The monitor presets at least one user-selectable operational parameter in response to the information element. In one embodiment, the application relates to emergency care and the user-selectable operational parameter is selected from the set of sensitivity and averaging time.

Another aspect of an application identification sensor is a method where a sensor is attached to a monitor and an information element is read. Data from the information element is associated with an application, and user-selectable parameters corresponding to the application are preset. In one embodiment, the application is identified as emergency related. In a particular embodiment, maximum sensitivity and minimum averaging time are selected for processing a signal from the sensor.

An aspect of an application identification apparatus comprises a sensor configured to generate a physiological signal and a monitor capable of processing the physiological signal so as to measure a physiological parameter responsive to a constituent of pulsatile blood. The monitor has an application identification input. User-selectable operational parameters for said monitor have values responsive to the application identification input. In one embodiment, the application identification input is provided by an information element associated with the sensor and readable by the monitor. In another embodiment, the application identification input is provided by a user-actuated button associated with the monitor.

DETAILED DESCRIPTION OF THE PREFERRED EMBODIMENTS

Figure 1:
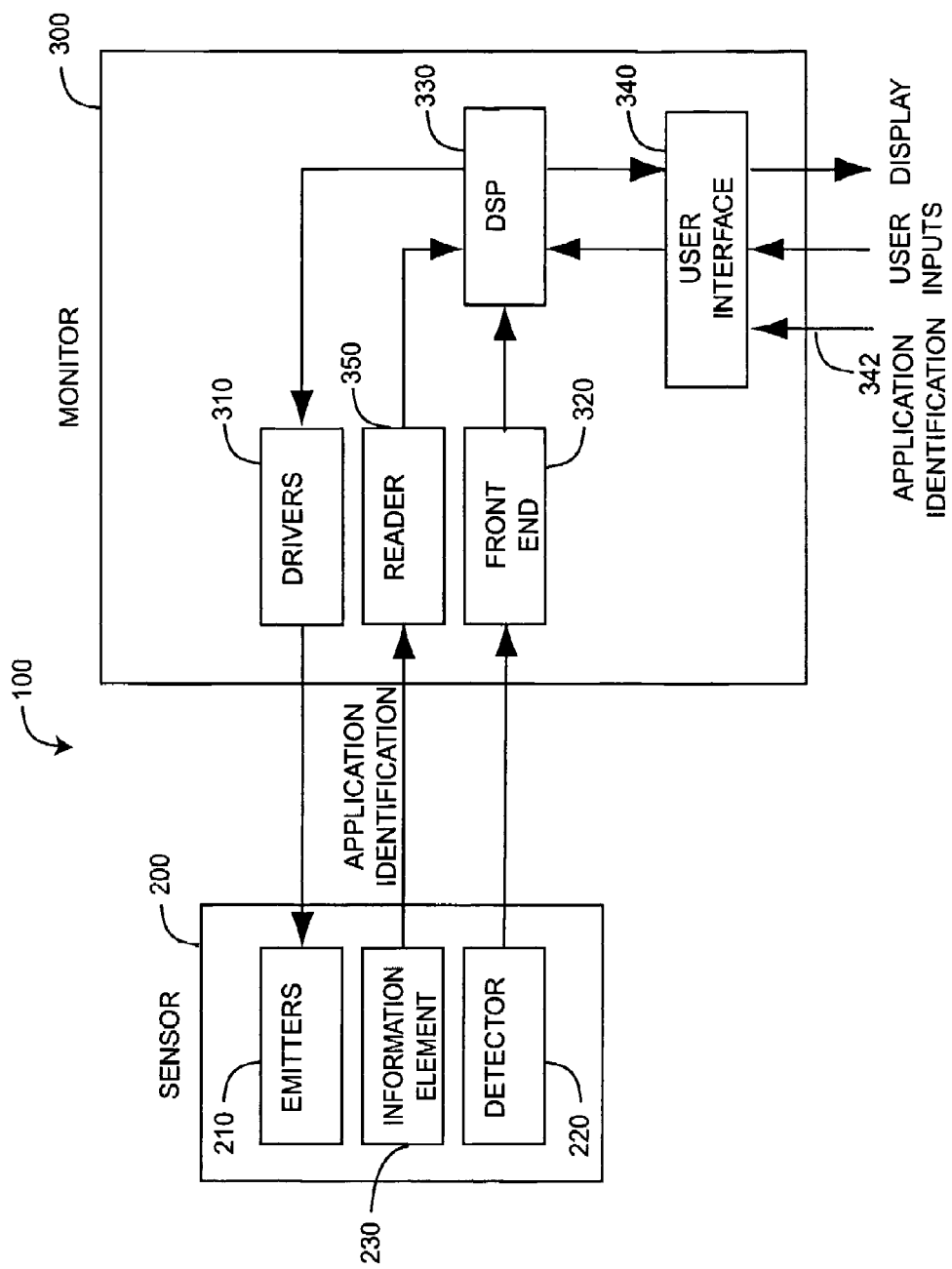
FIG. 1 is a block diagram a pulse oximetry system utilizing an application identification sensor or an application identification user input or both.

FIG. 1 illustrates a pulse oximetry system 100 incorporating an application identification sensor 200 and a monitor 300 adapted to recognize the sensor 200 accordingly. The sensor 200 has emitters 210 adapted to transmit light into a tissue site and a detector 220 adapted to receive light after absorption by the tissue site and to generate a detector signal in response, as is well known in the art. The monitor 300 has drivers 310 that activate the emitters 210 and a front-end 320 that conditions and digitizes the detector signal for input into a digital signal processor (DSP) 330, as is also well known in the art. The DSP 330 computes oxygen saturation and pulse rate and provides the results on a display. A user interface 340 allows a user to input selected operational parameters for the DSP 330. A pulse oximeter monitor is described in U.S. Pat. No. 6,699,194 entitled Signal Processing Apparatus and Method and U.S. Pat. No. 6,650,917 entitled Signal Processing Apparatus, which are assigned to Masimo Corporation, Irvine, Calif. and incorporated by reference herein. A user interface is described in U.S. Pat. No. 6,658,276 entitled Pulse Oximeter User Interface, which is assigned to Masimo Corporation, Irvine, Calif. and incorporated by reference herein.

Also shown in FIG. 1, the application identification sensor 200 also has an information element 230, and the monitor has a corresponding information element reader 350. Advantageously, the sensor 200 is manufactured with an information element 230 that identifies a particular application to the monitor 300. The monitor 300 presets one or more user-selectable operational parameters accordingly. This reduces or eliminates the need for user input of operational parameters specific to a particular application. In an alternative embodiment, the monitor 300 has an application identification button, switch or other user-actuated device 342 that causes the monitor 300 to preset one or more user-selectable operational parameters.

In one particularly advantageous embodiment, the application identification sensor 200 is manufactured, packaged and/or labeled for use in a trauma or emergency care situation, and the information element 230 is configured to identify that application or use to the monitor 300 accordingly. For example, when such a sensor 200 is connected to the monitor 300, the monitor 300 may select maximum sensitivity and minimum averaging time, providing hands-off optimum settings for these user-selectable operational parameters for a trauma care application. In an alternative embodiment, the monitor 300 has an application identification button 342 that is labeled for use in trauma or emergency care situations and that, when actuated, causes the monitor 300 to set user-selectable operational parameters accordingly.

For various applications, an application identification sensor 200 may indicate other user-selectable operational parameters relating to monitor alarms, displays, outputs and general characteristics to name a few. Alarm parameters may include alarm limits, delay and volume, for example. Display parameters may regard numeric, plethysmograph and trend formats to name a few. Output parameters may include, for instance, the analog output and alarm output types and digital output data formats. General characteristics may include operational modes such as maximum sensitivity and minimum averaging time cited above. General characteristics may also include averaging mode, such as described in U.S. Pat. No. 6,430,525 entitled Variable Mode Averager, which is assigned to Masimo Corporation, Irvine, Calif. and incorporated by reference herein. General characteristics may further include, for example, user key lock-out and password entry to enable user keys and other monitor functions.

An application identification sensor has been disclosed in detail in connection with various embodiments. These embodiments are disclosed by way of examples only and are not to limit the scope of the claims that follow. For example, although an application identification sensor has been described with respect to a pulse oximetry system, a sensor having an information element that identifies an application to a monitor can be utilized in systems capable of measuring physiological parameters other than or in addition to oxygen saturation and pulse rate. One of ordinary skill in art will appreciate many other variations and modifications.

What is claimed is:

1. An application identification sensor comprising:
   a plurality of emitters configured to transmit light into a tissue site;
   a detector configured to receive said light after tissue absorption, said detector generating a signal responsive to the intensity of said light and communicating said signal to a monitor; and
   an information element readable by said monitor so as to identify a sensor application, said monitor presetting at least one user-selectable operational parameter in response to said information element.

2. The application identification sensor according to claim 1 wherein:
   said application relates to emergency care, and
   said user-selectable operational parameter is selected from the set of sensitivity and averaging time.

3. An application identification sensor method comprising the steps of:
   attaching a sensor to a monitor;
   reading an information element corresponding to said sensor;
   associating data from said information element with an application; and
   presetting user-selectable parameters in said monitor corresponding to said application.

4. The application identification sensor method according to claim 3 wherein said associating step comprises the substep of identifying said application as emergency related.

5. The application identification sensor method according to claim 4 wherein said presetting step comprises the substep of selecting maximum sensitivity and minimum averaging time for processing a signal from said sensor.

6. An oximeter system capable of pre-configuring itself for differing operational conditions, the oximeter system comprising:
   a noninvasive optical sensor configured to generate an intensity signal indicative of one or more physiological parameters responsive to a constituent of pulsatile blood of a patient being monitored;
   an information element; and
   a processor responsive to said intensity signal to determine measurements of said parameters, said processor also responsive to said information element to pre-configure one or more of a plurality of user-selectable configurations.

7. The oximeter system of claim 6, wherein said user-selectable configurations include configuration of alarm characteristics.

8. The oximeter system of claim 7, wherein said alarm characteristics comprise at least one of alarm limits, alarm delays, and alarm volume.

9. The oximeter system of claim 6, wherein said user-selectable configurations include configuration of display characteristics.

10. The oximeter system of claim 9, wherein said display characteristics comprise at least one of numerical indicia of a display, plethysmographic indicia of said display, and trend indicia of said display.

11. The oximeter system of claim 6, wherein said user-selectable configurations include configuration of output characteristics.

12. The oximeter system of claim 11, wherein said output characteristics comprise at least one of analog and digital output.

13. The oximeter system of claim 6, wherein said user-selectable configurations include configuration of operational modes.

14. The oximeter system of claim 13, wherein said operational modes include a sensitivity.

15. The oximeter system of claim 13, wherein said operational modes include an averaging mode.

16. The oximeter system of claim 6, wherein said user-selectable configurations include general monitor characteristics.

17. The oximeter system of claim 16, wherein said general monitor characteristics comprise user key configurations or lock-outs based on operator authentication.

* * * * *

(12) EX PARTE REEXAMINATION CERTIFICATE (9923rd)
United States Patent
Al-Ali et al.

(10) Number: US 7,438,683 C1
(45) Certificate Issued: Nov. 6, 2013

(54) APPLICATION IDENTIFICATION SENSOR

(75) Inventors: Ammar Al-Ali, Tustin, CA (US); Massi E. Kiani, Laguna Niguel, CA (US); Walter M. Weber, Laguna Hills, CA (US)

(73) Assignee: Masimo Corporation, Irvine, CA (US)

Reexamination Request:
No. 90/012,546, Oct. 25, 2012

Reexamination Certificate for:
Patent No.: 7,438,683
Issued: Oct. 21, 2008
Appl. No.: 11/071,875
Filed: Mar. 3, 2005

Related U.S. Application Data

(60) Provisional application No. 60/549,996, filed on Mar. 4, 2004.

(51) Int. Cl.
*A61B 5/00* (2006.01)

(52) U.S. Cl.
USPC ............................................. 600/309; 600/323

(58) Field of Classification Search
None
See application file for complete search history.

(56) References Cited

To view the complete listing of prior art documents cited during the proceeding for Reexamination Control Number 90/012,546, please refer to the USPTO's public Patent Application Information Retrieval (PAIR) system under the Display References tab.

*Primary Examiner* — Robert Nasser

(57) ABSTRACT

An application identification sensor comprises a plurality of emitters configured to transmit light into a tissue site and a detector configured to receive the light after tissue absorption. The detector generates a signal responsive to the intensity of the light and communicates the signal to a monitor. An information element is readable by the monitor so as to identify a sensor application. The monitor presets at least one user-selectable operational parameter in response to the information element.

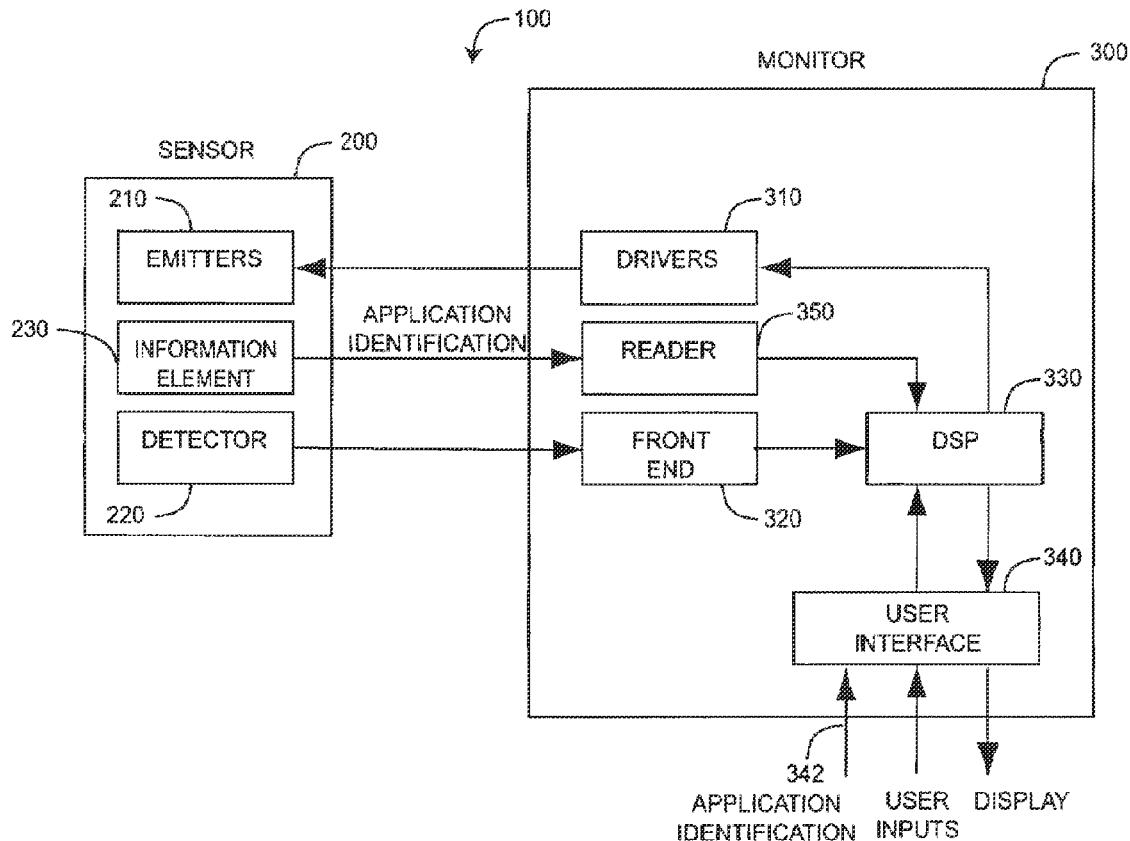

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 6-17 is confirmed.

Claims 1-5 and 18-20 are cancelled.

New claim 21 is added and determined to be patentable.

*21. An application identification sensor method pre-configuring an oximeter system for differing operational conditions, the oximeter system including a noninvasive optical sensor, an information element, and a monitor including a signal processor, the method comprising the steps of:*

*attaching said noninvasive optical sensor to said monitor, the sensor configured to generate an intensity signal indicative of one or more physiological parameters responsive to a constituent of pulsatile blood of a patient being monitored;*

*reading said information element corresponding to said sensor;*

*using said signal processor of said monitor, determining measurements of said physiological parameters, said measurements responsive to said intensity signal;*

*associating data from said information element with an application, said application being one of said differing operational conditions; and*

*presetting user-selectable parameters in said processor of said monitor corresponding to said application to pre-configure said monitor for said one of said differing operational conditions.*

\* \* \* \* \*